United States Patent [19]

Haugwitz

[11] 4,217,358
[45] Aug. 12, 1980

[54] SUBSTITUTED PHENYLGUANIDINES AND METHOD

[75] Inventor: Rudiger D. Haugwitz, Titusville, N.J.

[73] Assignee: E. R. Squibb & Sons, Inc., Princeton, N.J.

[21] Appl. No.: 31,249

[22] Filed: Apr. 18, 1979

[51] Int. Cl.² ............... A61K 31/40; A61K 31/445; C07D 209/48; C07D 207/04

[52] U.S. Cl. .................. 424/274; 260/326 S; 260/326.41; 546/220; 560/9; 560/13; 424/267; 424/300

[58] Field of Search ............... 260/326.41, 326 S; 546/220; 560/13, 25, 9; 424/267, 274, 300

[56] References Cited

U.S. PATENT DOCUMENTS

| 3,993,682 | 11/1976 | Kolling | 260/470 |
|---|---|---|---|
| 4,024,176 | 5/1977 | Kolling | 260/470 |
| 4,032,655 | 6/1977 | Kolling | 424/300 |

FOREIGN PATENT DOCUMENTS

| 851920 | 8/1977 | Belgium. |
| 860709 | 10/1978 | Belgium. |
| 2630847 | 1/1978 | Fed. Rep. of Germany. |
| 765531 | 10/1970 | France. |

Primary Examiner—Donald G. Daus
Assistant Examiner—M. C. Eakin
Attorney, Agent, or Firm—Lawrence S. Levinson; Burton Rodney

[57] ABSTRACT

Phenylguanidine derivatives are provided having the structure

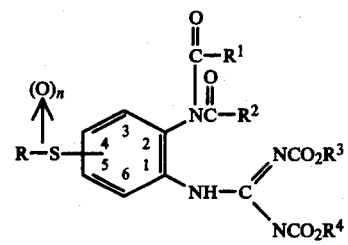

wherein R is lower alkyl, cycloalkyl, cycloalkylalkyl, lower alkenyl, lower alkynyl, phenyl or benzyl; $R^1$ and $R^2$ may be the same or different and are lower alkyl or $R^1$ and $R^2$ may be taken together to form an alkylene linking group of 2 or 3 carbons or an o-phenylene group; $R^3$ and $R^4$ are the same or different and are lower alkyl, benzyl or phenyl; and n is 0 or 1. These compounds are useful as anthelmintic agents.

13 Claims, No Drawings

SUBSTITUTED PHENYLGUANIDINES AND METHOD

DESCRIPTION OF THE INVENTION

The present invention relates to phenylguanidine derivatives which are useful as anthelmintic agents and have the structure

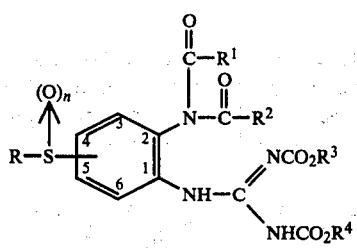

wherein R is lower alkyl, cycloalkyl, cycloalkylalkyl, lower alkenyl, lower alkynyl, phenyl, or benzyl; $R^1$ and $R^2$ may be the same or different and are lower alkyl or $R^1$ and $R^2$ taken together may form a cyclic-aliphatic imide (that is $R^1$ and $R^2$ represent an alkylene group of 2 or 3 carbons) or an aromatic imide (that is $R^1$ and $R^2$ are an o-phenylene moiety ring); $R^3$ and $R^4$ are the same or different and are lower alkyl, benzyl or phenyl; and n is 0 or 1.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "cycloalkyl" includes cyclic hydrocarbon groups containing 3 to 12 carbons, which include cyclopropyl, cyclobutyl, cyclopentyl, cyclohexyl, cycloheptyl, cyclooctyl, cyclodecyl and cyclododecyl, any of which groups may be substituted with 1, 2, 3 or 4 halogen and/or 1, 2, 3, or 4 lower alkyl groups.

The term "cycloalkylalkyl" refers to any of the above cycloalkyl groups linked to a lower alkyl group as defined above.

The term "lower alkenyl" refers to an unsaturated hydrocarbon group having from 3 to 6 carbon atoms and a single carbon-carbon double bond. Typical alkenyl groups include, for example, 2-propenyl, 1-propenyl, 1-butenyl, 2-butenyl, 3-butenyl, and the like.

The term "lower alkynyl" refers to an unsaturated hydrocarbon group having from 3 to 6 carbon atoms, and a single carbon-carbon triple bond. Typical alkynyl groups include, for example, 1-propynyl, 1-butynyl, 2-propynyl, 2-butynyl, 3-butynyl, and the like.

Preferred are those compounds wherein R is lower alkyyl, $R^1$ and $R^2$ together form a 2 or 3 carbon alkylene chain, $R^3$ and $R^4$ are lower alkyl and n is 0 or 1.

Thus, the compounds of the invention include the following:

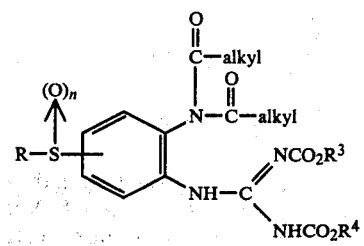

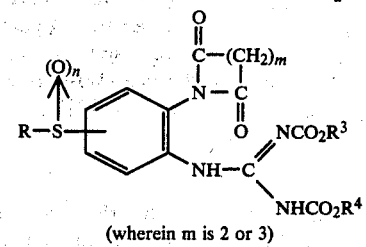

(wherein m is 2 or 3)

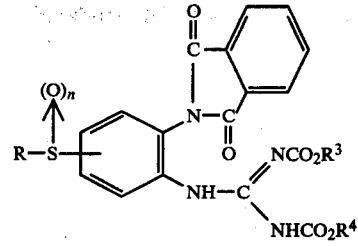

The compounds of structure I may be prepared by reacting anilines of the structure V

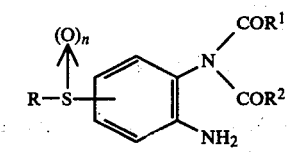

with an S-methylisothiourea VI

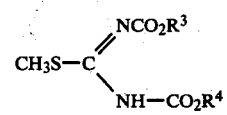

optionally, in the presence of an acid such as p-toluenesulfonic acid or acetic acid. The above reaction is preferably carried out at temperatures ranging from about 50° to about 100° C. for periods ranging from about 1 to about 5 hours.

The aniline of structure V may be prepared by reduction of the nitro derivatives VII

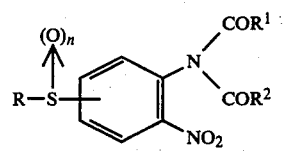

The reduction may be carried out catalytically with hydrogen and platinum or chemically with dithionite, or zinc and an acid such as hydrochloric acid or acetic acid.

The formula VII nitro derivatives are synthesized by reacting compounds of the structure VIII

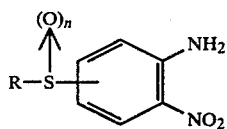 VIII with an appropriate reagent depending upon the type of R¹, R² group to be present in the formula VII compound. Thus, diacylation of o-nitroanilines VIII using an acid anhydride IX, for example, acetic anhydride, in the presence of concentrated acid, such as, concentrated sulfuric acid will yield the diacyl-o-nitroanilines VII (J J. Blanksma, Chem. Z, 1909, II, 1219).

(alkylCO)₂O          (IX)

Reaction of VIII with acid anhydrides X, such as succinic anhydride, glutaric anhydride, or their corresponding di-acid chloride, will yield imides XI

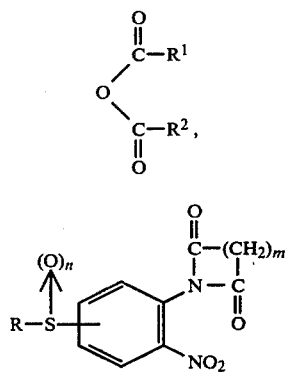 X

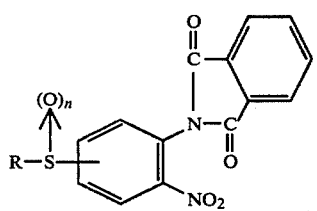 XI while reaction of VIII with phthalic anhydride will yield the aromatic imide XII

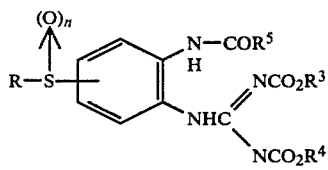 XII

Compounds of structures I, III and IV may also be prepared by cyclodehydrating acid derivatives

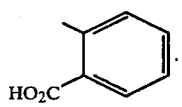 XIII wherein R⁵ is —(CH₂)$_m$CO₂H or

Compounds of the structure VIII are prepared by reacting XIV

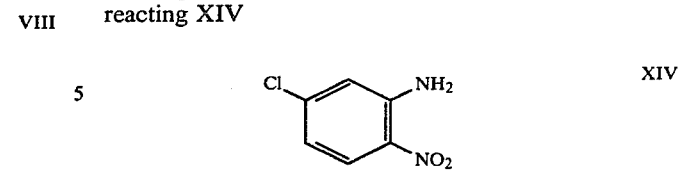 XIV with the appropriate thiol XV or preferably, the thiol salt to furnish VIII, where n is 0.

R—S$^\ominus$          XV

Compounds of structure VIII (n=0) can also be prepared by reducing thiocyanates XVI with sodium borohydride and then alkylating the resulting thiol XVII with the requisite halo-derivative RX.

NCS—⟨ ⟩—NO₂ / NH₂   $\xrightarrow{NaBH_4}$   HS—⟨ ⟩—NO₂ / NH₂

XVI                         XVII

XVII  $\xrightarrow{RX}$  VIII  n = 0

The compounds of formula I wherein n is 1 may be prepared by oxidizing compounds of formula I wherein n is 0, utilizing one equivalent of an oxidizing agent such as m-chloroperbenzoic acid, sodium m-periodate or hydrogen peroxide in acetic acid. Addition routes are outlined in Houben-Weyl's *Methoden Der Organischen Chemie*, Vol. 9, pp. 211–217 (1955), C. Thieme Verlag, Stuttgart.

The oxidation step may also be introduced at an earlier stage in the reaction sequence. For example, nitro derivative VII where n is 0, or nitro derivative VIII where n is 0 may be oxidized with any of the aforementioned oxidizing agents to give VII or VIII, respectively, wherein n is 1.

The acid derivatives of structure XIII are prepared by reacting a compound of the structure VIII with a cyclic dicarboxylic acid anhydride, such as succinic anhydride or glutaric anhydride, or phthalic anhydride, in the presence of a strong acid, such as sulfuric acid and an aromatic solvent, such as toluene, benzene, chloroform or xylene, preferably at reflux, to form an acid of the structure XVIII or XIX

XVIII                         XIX

Refluxing solutions of XVIII or XIX in solvents such as benzene or toluene will yield the cyclized products XI or XII.

In certain instances, the compounds of formula I form physiologically acceptable acidaddition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep. The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or may be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit or scope thereof. All temperatures are in degrees centigrade.

EXAMPLE 1

4-[[2-[[[(Methoxycarbonyl)amino][(methoxycarbonyl)-imino]methyl]amino]-5-[(1-methylpropyl)thio]phenyl]amino]-4-oxobutanic acid

A.

[[(Methoxycarbonyl)amino](methylthio)-methylene]-carbamic acid, methyl ester

To a solution of 112 g of S-methyl-2-thiourea sulfate in 200 ml of water at 0° C. there is added concurrently 260 ml of 25% NaOH and 160 ml of methyl chloroformate at such a rate that the pH remains between 7 and 8 as monitored by a pH meter. After the addition is complete the mixture is stirred for an additional 2 hours at room temperature. Then 400 ml of water is added and the mixture is extracted with dichloromethane. The organic layers are combined, dried over magnesium sulfate, and evaporated in vacuo to give a white solid. Crystallization from methanol yields 60.4 g, m.p. 99°–101° C.

B.

4-[[2-[[[Methoxycarbonyl)amino][(methoxycarbonyl)imino]methyl]amino]-5-[(1-methylpropyl)thio]phenyl]amino]-4-oxobutanic acid A mixture of 11.2 g (0.05 mole) of 5-[(2-methylpropyl)thio]-2-nitroaniline, 5.0 g of succinic anhydride and 0.5 ml of $H_2SO_4$ is refluxed in 100 ml of toluene for 1 hour. The mixture is fitered off and evaporated in vacuo. The residue is crystallized from $Et_2O$ to yield 7.5 g, m.p. 135°–140° C.

A mixture of 6.0 g (0.02 mole) of the above nitro compound and 0.6 g of $PtO_2$ in 200 ml of absolute ethanol is reduced on the Parr hydrogenator at 50 psi until the theoretical amount of hydrogen is absorbed. The mixture is filtered and the solvent is removed in vacuo to leave an oil which is used immediately in the following reaction.

To a solution of the above amine in 200 ml of methanol there is added 4.0 g (0.02 mole) of [[(methoxycarbonyl)amino](methylthio)methylene]-carbamic acid, methyl ester and 1 ml of acetic acid and the mixture is refluxed for 3 hours. The reaction mixture is filtered hot, reduced in volume in vacuo and cooled. The resulting solid is filtered off, washed with $Et_2O$, and crystallized from EtOH to yield 0.9 g, m.p. 166°–168° C.

EXAMPLE 2

[[[2-(2,5-Dioxo-1-pyrrolidinyl)-4-[(1-methylpropyl)-thio]phenyl]amino][(methoxycarbonyl)amino]methyl]-carbamic acid, methyl ester A mixture of 11.2 g (0.05 mole) of 5-[(2-methylpropyl)thio]-2-nitroaniline and 5.0 g of succinic anhydride is refluxed in 100 ml of benzene for 1 hour. The mixture is filtered and the solvent is removed in vacuo.

The residue is crystallized from Et$_2$O to yield 11.1 g, m.p. 98°–100° C.

A mixture of 9.0 g (0.03 mole) of the above nitro compound and 1.0 g of PtO$_2$ in 200 ml of absolute ethanol is reduced on the Parr hydrogenator at 50 psi until the theoretical amount of hydrogen is absorbed. The mixture is filtered and the solvent is removed in vacuo to leave an oil which is used immediately in the following reaction.

To a solution of the above amine in 200 ml of methanol there is added 6.0 g (0.03 mole) of [[(methoxycarbonyl)amino](methylthio)methylene]-carbamic acid, methyl ester and 1 ml of acetic acid and the mixture is refluxed for 3 hours. The reaction mixture is filtered hot, reduced in volume in vacuo and Et$_2$O is added. On standing, crystals which separate are filtered off to yield 2.1 g, m.p. 138°–140° C.

EXAMPLE 3

[[[2-(2,5-Dioxo-1-pyrrolidinyl)-4-[(1-methylpropyl)-sulfinyl]phenyl]amino][(methoxycarbonyl)amino]methyl]-carbamic acid, methyl ester To a solution of 3.9 g (0.01 mole) of [[[2-(2,5-dioxo-1-pyrrolidinyl)-4-[(2-methylpropyl)-thio]phenyl]amino][-(methoxycarbonyl)amino]methylene]carbamic acid, methyl ester in 250 ml of chloroform there is added 2.0 g (0.01 mole) of 85% m-chloroperoxybenzoic acid in 10 ml of chloroform with ice bath cooling. The reaction mixture is allowed to warm to room temperature and then stirred for 3 hours. The reaction mixture is washed with aqueous potassium carbonate and then with water until the pH is 7. The organic layer is dried (MgSO$_4$), filtered, and evaporated in vacuo. The residue is crystallized from ethanol to yield the title compound.

EXAMPLE 4

[[[2-(N,N-Diacetylamino)-4-[(1-methylpropyl)-thio]-phenyl]amino][(methoxycarbonyl)amino]methyl]carbamic acid, methyl ester To 5 g of 2-nitro-5(2-methylpropyl)thio aniline, there is added 50 ml of acetic anhydride and several drops of concentrated sulfuric acid. The mixture is refluxed for several hours, the excess acetic anhydride evaporated, and the resulting residue is crystallized to furnish 2-nitro-5-(2-methylpropyl)thio-N,N-diacetyl aniline.

A mixture of 9.0 g (0.03 mole) of the above nitro compound and 1.0 g of PtO$_2$ in 200 ml of absolute ethanol is reduced on the Parr hydrogenator at 50 psi until the theoretical amount of hydrogen is absorbed. The mixture is filtered and the solvent is removed in vacuo to leave an oil which is used immediately in the following reaction.

To a solution of the above amine in 200 ml of methanol there is added 6.0 g (0.03 mole) of [[(methoxycarbonyl)amino](methylthio)methylene]-carbamic acid, methyl ester and 1 ml of acetic acid and the mixture is refluxed for 3 hours. The reaction mixture is filtered hot, reduced in volume in vacuo and Et$_2$O is added. On standing, the title compound crystallizes.

EXAMPLE 5

[[[2-(N,N-Diacetylamino)-5-[(2-methylpropyl)-sulfinyl]phenyl]amino][(methoxycarbonyl)amino]-methyl]carbamic acid, methyl ester To a solution of 3.9 g (0.01 mole) of [[[2-(N,N-diacetylamino)-4-[(1-methylpropyl)thio]phenyl]amino][methoxycarbonyl)amino]methyl]carbamic acid, methyl ester in 250 ml of chloroform there is added 2.0 g (0.01 mole) of 85% m-chloroperoxybenzoic acid in 10 ml of chloroform with ice bath cooling. The reaction mixture is allowed to warm to room temperature and then stirred for 3 hours. The reaction mixture is washed with aqueous potassium carbonate and then with water until the pH is 7. The organic layer is dried (MgSO$_4$), filtered, and evaporated in vacuo. The residue is crystallized from ethanol to yield the title compound.

EXAMPLES 6 to 21

Following the procedure of Examples 1 and 2 but substituting for 5-[(2-methylpropyl)thio]-2-nitroaniline, the aniline derivative shown in Column I of Table I set out below, substituting for succinic anhydride, the compound shown in Column II, and substituting for [[(methoxycarbonyl)-amino](methylthio)methyl]carbamic acid, methyl ester, the compound shown in Column III, the product in accordance with the present invention shown in Column IV is obtained.

TABLE I

| | Column I | | Column II | Column III | Column IV | | | | |
|---|---|---|---|---|---|---|---|---|---|
| Ex. No. | R (position of R—S) | | R$^1$   R$^2$ | R$^3$   R$^4$ | R | (position of R—S) | R$^1$ | R$^2$ | R$^3$   R$^4$ |
| 6. | (CH$_3$)$_2$CHCH$_2$ (5) | | —CH$_2$CH$_2$ | CH$_3$   CH$_3$ | as in Column I | (4) | as in Column II | | as in Column III |
| 7. | ▷—(5) | | —CH$_2$CH$_2$CH$_2$— | CH$_3$   CH$_3$ | | (4) | | | |
| 8. | CH$_2$=CH—CH$_2$ (5) | | | C$_6$H$_5$   C$_6$H$_5$ | | (4) | | | |

TABLE I-continued

| | Column I | Column II | Column III | Column IV |
|---|---|---|---|---|

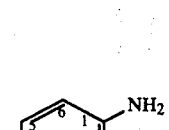

| Ex. No. | R (position of R—S) | R$^1$ R$^2$ | R$^3$ | R$^4$ | R | (position of R—S) | R$^1$ R$^2$ | R$^3$ | R$^4$ |
|---|---|---|---|---|---|---|---|---|---|
| 9. | (CH$_3$)$_2$CH (5) | —CH$_2$CH$_2$— | CH$_3$ | CH$_3$ | | (4) | | | |
| 10. | CH≡C—CH$_2$—(4) | —CH$_2$CH$_2$— | CH$_2$C$_6$H$_5$ | CH$_2$C$_6$H$_5$ | as in Column I | (5) | as in Column II | as in Column III | |
| 11. | Cl Cl <br>  \/ <br>  /\—CH$_2$— (5) | —CH$_2$CH$_2$CH$_2$— | C$_2$H$_5$ | C$_2$H$_5$ | | (4) | | | |
| 12. | ☐—CH$_2$— (5) | —CH$_2$CH$_2$— | CH$_3$ | CH$_3$ | | (4) | | | |
| 13. | C$_6$H$_5$CH$_2$ (4) | —CH$_2$CH$_2$— | CH$_3$ | CH$_3$ | | (5) | | | |
| 14. | Cl Cl <br>  \/ <br>  /\—CH$_2$— (5) <br>   CH$_3$ | (o-phenylene) | C$_2$H$_5$ | C$_2$H$_5$ | | (4) | | | |
| 15. | (CH$_3$)$_2$CH— (5) | —CH$_2$CH$_2$CH$_2$— | C$_6$H$_5$ | C$_6$H$_5$ | | (4) | | | |
| 16. | (CH$_3$)$_2$CHCH$_2$— (5) | (o-phenylene) | CH$_3$ | CH$_3$ | | (4) | | | |
| 17. | △—CH$_2$ (5) | —CH$_2$CH$_2$CH$_2$— | CH$_3$ | CH$_3$ | | (4) | | | |
| 18. | CH$_2$=CHCH$_2$ (5) | —CH$_2$CH$_2$— | C$_6$H$_5$ | C$_6$H$_5$ | | (4) | | | |
| 19. | ☐—(5) | —CH$_2$CH$_2$— | CH$_3$ | CH$_3$ | | (4) | | | |
| 20. | C$_6$H$_5$ (5) | —CH$_2$CH$_2$— | CH$_3$ | CH$_3$ | | (4) | | | |
| 21. | CH$_2$=CH—CH$_2$ (5) | —CH$_2$CH$_2$— | CH$_2$C$_6$H$_5$ | CH$_2$C$_6$H$_5$ | | (4) | | | |

EXAMPLES 22 TO 31

Following the procedure of Example 4, but substituting for 2-nitro-5-(2-methylpropyl)-thioaniline, the aniline derivative shown in Column I of Table II set out below, substituting for acetic anhydride, the compound shown in Column II, and substituting for [[(methoxycarbonyl)amino]-(methylthio)methyl]carbamic acid, methyl ester, the compound shown in Column III, the product in accordance with the present invention shown in Column IV is obtained.

TABLE II

| | Column I | Column II | Column III | Column IV |
|---|---|---|---|---|

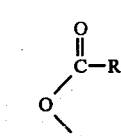

| Ex. No. | R (position of R—S) | alkyl | R$^3$ | R$^4$ | R | (position of R—S) | alkyl | R$^3$ | R$^4$ |
|---|---|---|---|---|---|---|---|---|---|
| 22. | i-C$_3$H$_7$ (5) | CH$_3$ | CH$_3$ | CH$_3$ | as in Column I | (4) | as in Column II | as in Column III | |
| 23. | ▷—CH$_2$ (5) | C$_2$H$_5$ | C$_2$H$_5$ | C$_2$H$_5$ | | (4) | | | |
| 24. | CH$_2$=CH—CH$_2$ (5) | CH$_3$ | CH$_3$ | CH$_3$ | | (4) | | | |
| 25. | (CH$_3$)$_2$CHCH$_2$ (5) | C$_2$H$_5$ | CH$_2$C$_6$H$_5$ | CH$_2$C$_6$H$_5$ | | (4) | | | |
| 26. | CH≡C—CH$_2$— (4) | n-C$_3$H$_7$ | C$_6$H$_5$ | C$_6$H$_5$ | | (5) | | | |
| 27. | Cl Cl <br>  \/ <br>  /\—CH$_2$— (5) | n-C$_4$H$_9$ | CH$_3$ | CH$_3$ | | (4) | | | |

TABLE II-continued

| | Column I | Column II | Column III | | Column IV | | | |
|---|---|---|---|---|---|---|---|---|
| | 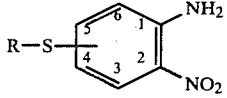 | (alkylCO)₂O | 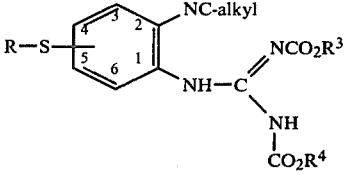 | |  | | | |
| Ex. No. | R(position of R—S) | alkyl | $R^3$ | $R^4$ | R (position of R—S) | alkyl | $R^3$ | $R^4$ |
| 28. | —(5) | $C_5H_{11}$ | $C_2H_5$ | $C_2H_5$ | as in Column I | (4) | as in Column II | as in Column III |
| 29. | $C_6H_5CH_2$ (4) | $CH_3$ | $CH_3$ | $CH_3$ | | (5) | | |
| 30. |  | $C_2H_5$ | $CH_3$ | $CH_3$ | | (4) | | |
| 31. | $C_6H_5$ (5) | i-$C_3H_7$ | $C_2H_5$ | $C_2H_5$ | | (4) | | |

EXAMPLES 32 TO 57

Following the procedure of Example 3 except substituting the compounds of Examples 6 to 31 for the [[[2-(2,5-dioxo-1-pyrrolidinyl)-4-[(1-methylpropyl)thio]-phenyl]amino][methoxycarbonyl)amino]methyl]carbamic acid, methyl ester, the corresponding sulfoxides of the compounds of Examples 6 to 31 are obtained.

What is claimed is:

1. A compound of the structure

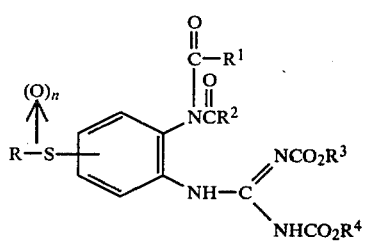

wherein R is lower alkyl, cycloalkyl having 3 to 12 carbons, cycloalkyl-lower alkyl having 3 to 12 carbons in the cycloalkyl portion, lower alkenyl, lower alkynyl, phenyl or benzyl, $R^1$ and $R^2$ may be the same or different and are lower alkyl of $R^1$ and $R^2$ taken together may form an alkylene linking group of 2 or 3 carbons or an o-phenylene group; $R^3$ and $R^4$ are the same or different and are lower alkyl, benzyl or phenyl, and n is 0 or 1, and physiologically acceptable salts thereof.

2. The compound as defined in claim 1 wherein n is 0.

3. The compound as defined in claim 1 wherein n is 1.

4. The compound as defined in claim 1 wherein $R^1$ is lower alkyl and $R^2$ is lower alkyl.

5. The compound as defined in claim 1 having the structure

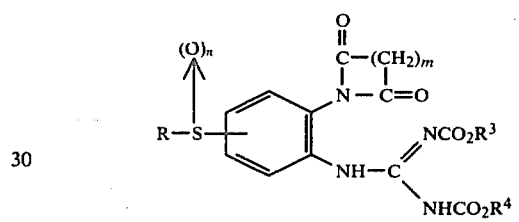

wherein m is 2 or 3.

6. The compound as defined in claim 1 having the structure

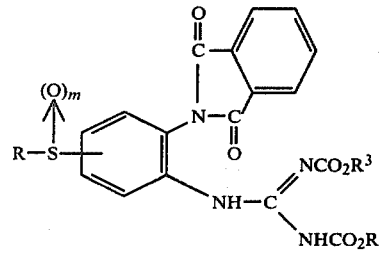

7. The compound as defined in claim 1 wherein R is lower alkyl, $R^1$ and $R^2$ are taken together to form $(CH_2)_2$ or $(CH_2)_3$, and $R^3$ and $R^4$ are lower alkyl.

8. The compound as defined in claim 1 having the name [[[2-(2,5-dioxo-1-pyrrolidinyl)-4-[(1-methylpropyl)thio]phenyl]amino][(methoxycarbonyl)amino]methyl]carbamic acid, methyl ester.

9. The compound as defined in claim 1 having the name [[[2-(2,5-dioxo-1-pyrrolidinyl)-4-[(1-methylpropyl)sulfinyl]phenyl]amino][(methoxycarbonyl)amino]methyl]carbamic acid, methyl ester.

10. An anthelmintic composition comprising a therapeutic amount of a compound as defined in claim 1 and a pharmaceutically acceptable carrier therefor.

11. A method for treating or preventing helminth infestation in mammalian hosts which comprises administering to a mammal a therapeutic amount of an anthelmintic composition as defined in claim 10.

12. The method as defined in claim 11 wherein said composition is administered orally or parenterally.

13. The method as defined in claim 12 wherein said composition is administered parenterally.

* * * * *

UNITED STATES PATENT AND TRADEMARK OFFICE
CERTIFICATE OF CORRECTION

PATENT NO. : 4,217,358
DATED : August 12, 1980
INVENTOR(S) : Rudiger D. Haugwitz It is certified that error appears in the above-identified patent and that said Letters Patent are hereby corrected as shown below:

Column 11, line 59, after "alkyl", "of" should read --or--.

Signed and Sealed this

Twenty-third Day of December 1980

[SEAL]

Attest:

SIDNEY A. DIAMOND

Attesting Officer

Commissioner of Patents and Trademarks